United States Patent
Boday et al.

(10) Patent No.: US 9,592,470 B2
(45) Date of Patent: Mar. 14, 2017

(54) SULFUR SCAVENGING MATERIALS FOR FILTERS AND COATINGS

(71) Applicant: International Business Machines Corporation, Armonk, NY (US)

(72) Inventors: Dylan J. Boday, Tucson, AZ (US); Jeannette M. Garcia, San Jose, CA (US); James L. Hedrick, Pleasanton, CA (US); Rudy J. Wojtecki, San Jose, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 296 days.

(21) Appl. No.: 14/288,319

(22) Filed: May 27, 2014

(65) Prior Publication Data

US 2015/0343352 A1 Dec. 3, 2015

(51) Int. Cl.

| | |
|---|---|
| *B01D 39/04* | (2006.01) |
| *A61L 9/00* | (2006.01) |
| *C08G 73/02* | (2006.01) |
| *B01D 53/48* | (2006.01) |
| *C09D 5/08* | (2006.01) |
| *C09D 179/04* | (2006.01) |
| *C09D 179/02* | (2006.01) |
| *C10L 3/10* | (2006.01) |
| *B01D 39/08* | (2006.01) |
| *B01D 24/02* | (2006.01) |
| *B01D 24/36* | (2006.01) |
| *B01D 53/02* | (2006.01) |
| *B01D 53/38* | (2006.01) |
| *B01J 20/22* | (2006.01) |
| *B01J 20/28* | (2006.01) |
| *C08G 73/06* | (2006.01) |
| *C10G 25/00* | (2006.01) |
| *B01D 53/46* | (2006.01) |
| *B01D 53/82* | (2006.01) |
| *B01D 53/92* | (2006.01) |
| *A61L 2/00* | (2006.01) |

(52) U.S. Cl.
CPC ............... *B01D 53/48* (2013.01); *A61L 2/00* (2013.01); *A61L 9/00* (2013.01); *B01D 24/02* (2013.01); *B01D 24/36* (2013.01); *B01D 39/04* (2013.01); *B01D 39/083* (2013.01); *B01D 53/02* (2013.01); *B01D 53/38* (2013.01); *B01D 53/46* (2013.01); *B01D 53/82* (2013.01); *B01D 53/92* (2013.01); *B01J 20/22* (2013.01); *B01J 20/28023* (2013.01); *B01J 20/28038* (2013.01); *C08G 73/02* (2013.01); *C08G 73/0638* (2013.01); *C08G 73/0644* (2013.01); *C09D 5/08* (2013.01); *C09D 5/082* (2013.01); *C09D 179/02* (2013.01); *C09D 179/04* (2013.01); *C10G 25/003* (2013.01); *C10L 3/103* (2013.01); *B01D 2257/30* (2013.01); *B01D 2257/302* (2013.01); *B01D 2257/304* (2013.01); *B01D 2257/306* (2013.01); *B01D 2258/0283* (2013.01); *B01D 2258/06* (2013.01); *C08G 2150/90* (2013.01); *C08G 2340/00* (2013.01); *C10L 2230/14* (2013.01); *C10L 2290/542* (2013.01); *C10L 2290/547* (2013.01)

(58) Field of Classification Search
USPC .................................................. 428/375, 394
See application file for complete search history.

(56) References Cited

U.S. PATENT DOCUMENTS

| | | |
|---|---|---|
| 2,889,277 A | 6/1959 | Hughes |
| 3,173,799 A | 3/1965 | George |
| 3,340,232 A | 9/1967 | Smith et al. |
| 3,598,748 A | 8/1971 | Hirosawa |
| 3,915,970 A | 10/1975 | Limaye et al. |
| 3,957,742 A | 5/1976 | Kveton |
| 4,010,028 A | 3/1977 | Irwin, Sr. et al. |
| 4,106,904 A | 8/1978 | Oude Alink et al. |
| 4,224,417 A | 9/1980 | Hajek et al. |

(Continued)

FOREIGN PATENT DOCUMENTS

| | | |
|---|---|---|
| CN | 101265255 A | 9/2008 |
| EP | 2636697 A1 | 9/2013 |

(Continued)

OTHER PUBLICATIONS

Amosa et al., Sulphide Scavengers in Oil and Gas Industry—A Review, NAFTA 61 (2) 85-92 (2010).

(Continued)

*Primary Examiner* — Tae H Yoon
(74) *Attorney, Agent, or Firm* — Patterson + Sheridan, LLP

(57) ABSTRACT

Materials which react with ("scavenge") sulfur compounds, such as hydrogen sulfide and mercaptans, are used to limit sulfur-induced corrosion. Filters and protective coatings including these materials, described broadly as polyhexahydrotriazines (PHT) and polyhemiaminals (PHA), are disclosed. Methods of using these materials to prevent corrosion are described. PHT and PHA materials have excellent thermal and mechanical properties for many applications as coatings and filtration media. Specifically, PHT and PHA materials react with sulfur compounds in such a manner as to incorporate sulfur atoms into the polymeric matrix, thus sequestering the sulfur atoms and allowing removal from fluids such as crude oil, natural gas, hydrocarbon combustion exhaust gases, sulfur polluted air and water. A coating PHT or PHA material on a component to be protected similarly reacts with sulfur compounds prior to sulfur being able to penetrate to the component.

20 Claims, 8 Drawing Sheets

(56) References Cited

U.S. PATENT DOCUMENTS

| | | |
|---|---|---|
| 4,225,481 A | 9/1980 | Wagner |
| 4,246,160 A | 1/1981 | Wagner et al. |
| 4,301,262 A | 11/1981 | Wagner et al. |
| 4,874,858 A | 10/1989 | Magistro |
| 4,877,451 A | 10/1989 | Winnik et al. |
| 4,978,512 A | 12/1990 | Dillon |
| 5,112,796 A | 5/1992 | Iannicelli |
| 5,554,349 A | 9/1996 | Rivers et al. |
| 5,674,377 A | 10/1997 | Sullivan, III et al. |
| 5,830,243 A | 11/1998 | Wolak et al. |
| 7,004,333 B2 | 2/2006 | Marcotullio et al. |
| 7,384,434 B2 | 6/2008 | Malfer et al. |
| 2009/0039018 A1 | 2/2009 | Jordi et al. |
| 2009/0076198 A1 | 3/2009 | Giesenberg et al. |
| 2009/0181240 A1 | 7/2009 | Williams et al. |
| 2010/0107476 A1 | 5/2010 | Cosimbescu |
| 2012/0049308 A1 | 3/2012 | Nishimura et al. |
| 2013/0192739 A1 | 8/2013 | Boday et al. |
| 2014/0171721 A1 | 6/2014 | Bertrand, III |
| 2015/0343421 A1 | 12/2015 | Boday et al. |
| 2015/0353584 A1 | 12/2015 | Boday et al. |
| 2015/0360173 A1 | 12/2015 | Boday et al. |

FOREIGN PATENT DOCUMENTS

| | | |
|---|---|---|
| GB | 928112 A | 6/1963 |
| GB | 1531578 A | 11/1978 |
| WO | 0166614 A2 | 9/2001 |
| WO | 0198388 A1 | 12/2001 |
| WO | 0226849 A1 | 4/2002 |

OTHER PUBLICATIONS

National Institute of Standards and Technology. Benzenamine, 4-bromo-N, N-dimethyl-. [online]. [retrieved on Jul. 24, 2015]. Retrieved from the Internet <URL: http://webbook.nist.gov/cgi/cbook.cgi?ID=586-77-6&Units=SI>, 2011 p. 1.

Search Report and Written Opinion mailed in International No. PCT/US15/33800 dated Aug. 21, 2015, 8 pages.

List of IBM Patents or Patent Applications Treated As Related, dated May 17, 2016.

Henri Ulrich et al., Reaction of Chloromethyl Ether with Primary Amines, May 1961, pp. 1637-1638.

Hemant S. Patel et al., Studies on Synthesis and Characterization of some Novel Aromatic Copolyesters based on s-Triazine, Iranian Polymer Journal, vol. 14, No. 12, 2005, pp. 1090-1098.

Fabian Suriano et al., Functionalized cyclic carbonates: from synthesis and metal-free catalyzed ring-opening polymerization to applications, Polymer Chemistry, The Royal Society of Chemistry, 2011, Received Jul. 6, 2010, Accepted Aug. 13, 2010, pp. 528-533.

Hydrogen Sulfide Management, Mitigation options in petroleum refining, storage and transportation, White Paper, Baker Hughes, pp. 1-12, 2011.

Wang Yulan et al., Synthesis and Properties of Poly-1, 3, 5-Triazines, Polymer Communications, No. 2, 1984, pp. 117-123.

John Markoff, Error at IBM Lap Finds New Family of Materials, New York Times, May 15, 2014, 4 pages.

Jeanette M. Garcia et al., Recyclable, Strong Thermosets and Organogels via Paraformaldehyde Condensation with Diamines, Science AAAS, vol. 344, May 16, 2014, pp. 732-735.

D.R. Anderson et al., Thermally resistance polymers containing the s-triazine ring, Journal of Polymer Science Part A-1: Polymer Chemistry, vol. 4, Issue 7, pp. 1689-1702, 1966.

T. Okita, Filter method for the determination of trace quantities of amines, mercaptans, and organic sulphides in the atmosphere, Atmospheric Environment (1967), vol. 4, Issue 1, Jan. 1970, pp. 93-102.

Raquel Lebrero et al., Odor abatement in biotrickling filters: Effect of the EBRT on methyl mercaptan and hydrophobic VOCs removal, Bioresource Technology, Special Issue: Innovative Researches on Algal Biomass, vol. 109, Apr. 2012, pp. 38-45.

Elbert, et al. "Conjugate Addition Reactions Combined with Free-Radical Cross-Linking for the Design of Materials for Tissue Engineering," Biomacromolecules 2001, 2, 430-441; Published on Web Mar. 3, 2001.

Ferrar, "Reactions of Formaldehyde With Aromatic Amines," J. Appl. Chem, 14, 1964, 389-399.

Geng, et al., "Nanoindentation behavior of ultrathin polymeric films," Polymer 46 (2005) 11768-11772; Available online Oct. 19, 2005.

Hiller, et al., "Laser-engravable hexahydrotriazine polymer networks," Mat Res Innovat (2002) 6:179-184.

Oliver, et al. "Measurement of hardness and elastic modulus by; instrumented indentation: Advances in understanding and; refinements to methodology," J. Mater. Res., vol. 19, No. 1, Jan 2004, 3-20.

Singh, et al., "Ultrasound mediated Green Synthesis of Hexa-hydro Triazines," J. Mater. Environ. Sci. 2 (4) (2011) 403-406.

Stafford, et al., "A buckling-based metrology for measuring; the elastic moduli of polymeric thin films," Nature Materials Aug. 3, 2004, 545-550;Published online: Jul. 11, 2004.

SULFUR SCAVENGING MATERIALS FOR FILTERS AND COATINGS

BACKGROUND

The present disclosure relates to materials that react with sulfur and sulfur-containing compounds, and more specifically to filtration of and corrosion protection against sulfur and sulfur-containing compounds.

Sulfur and sulfur containing compounds are often unwanted impurities in a variety of contexts. For example, sulfur is typically the most abundant element after carbon and hydrogen in crude oil. Sulfur in crude oil may be in the form of hydrogen sulfide (H2S) and/or thiols (also referred to as mercaptans), these materials, particularly H2S, may cause corrosion of metal pipeline components, storage tanks, and processing equipment. Additionally, any sulfur which remains in end-use fuels and lubricants may cause corrosion of, or other damage to, end-user equipment (e.g., engines, boilers, bearings, etc.). Combusted fuels or materials which include sulfur ultimately contribute to pollution as sulfur oxides ($SO_x$). Sulfur oxides cause harmful environmental effects and are particularly significant as contributors to air pollution. The various sulfur compounds emitted into the environment may corrode unprotected materials and be harmful to human health.

A need exists for devices and methods for removing sulfur and sulfur-containing compounds from an environment or otherwise protect materials against corrosion caused by sulfur and sulfur-containing compounds.

SUMMARY

In an embodiment of the present disclosure, a filter comprises a filtration medium including at least one of:

(a) a polyhexahydrotriazine (PHT) material having a plurality of trivalent hexahydrotriazine groups having the structure:

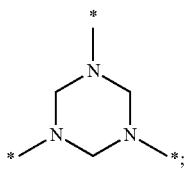

and
a plurality of divalent bridging groups of formula:

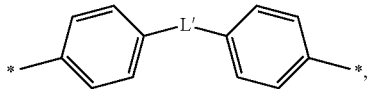

wherein
L' is a divalent linking group selected from the group consisting of *—O—*, *—S—*, *—N(R')—*, *—N(H)—*, *—R"—*, and combinations thereof, R' comprises at least 1 carbon and R" comprises at least one carbon, each starred bond of a given hexahydrotriazine group is covalently linked to a respective one of the divalent bridging groups, and each starred bond of a given bridging group is linked to a respective one of the hexahydrotriazine groups; and (b) a polyhemiaminal (PHA) material having a plurality of trivalent hemiaminal groups having the structure:

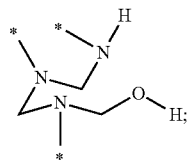

and
a plurality of divalent bridging groups of formula:

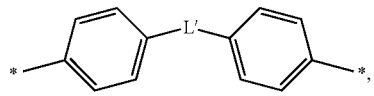

wherein
L' is a divalent linking group selected from the group consisting of *—O—*, *—S—*, *—N(R')—*, *—N(H)—*, *—R"—*, and combinations thereof, wherein R' comprises at least 1 carbon and R" comprises at least one carbon, each starred bond of a given hemiaminal group is covalently linked to a respective one of the divalent bridging groups, and each starred bond of a given bridging group is linked to a respective one of the hemiaminal groups.

Another embodiment of the present disclosure includes a method of removing sulfur compounds from a fluid, the method comprising placing the fluid including the sulfur compound into contact with at least one of a PHT material (as disclosed above) and a PHA material (as disclosed above).

Fluids in this context may include, without limitation, liquids, gases, and mixed-phase flows, streams, solutions, mixtures, and suspensions. Sulfur compounds in this context includes, without limitation, hydrogen sulfide ($H_2S$), thiols (R—SH, where R includes at least one carbon), and sulfur allotropes (e.g., "octosulfur" ($S_8$)).

In yet another embodiment of the present disclosure, a method of reducing sulfur-induced corrosion comprises coating a component with at least one of a PHT material (as disclosed above) and a PHA material (as disclosed above).

In this context, a component may be, without limitation, an electronic device, microchip, microelectronic device, printed circuit board, hard disk drive platter, a portion of fluid filter, and portion of a hydrocarbon (e.g., petroleum, natural gas, or petro-chemical) processing facility such as a pipe, pipeline, fluid pumping device, distillation column, a reaction vessel, or storage tank.

The above-described embodiments and other features and advantages of the present disclosure will be appreciated and understood by those skilled in the art from the following detailed description, drawings, and appended claims

DETAILED DESCRIPTION

Overview of PHA and PHT Materials

Figure 1:
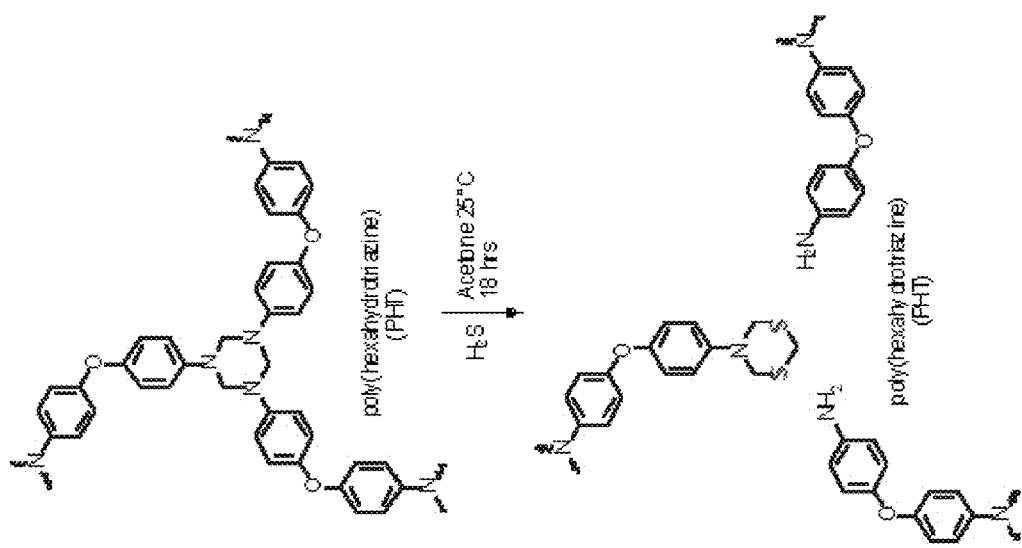
FIG. 1 depicts a reaction of polyhexahydrotriazine (PHT) material with a sulfur compound.

Polyhemiaminal (PHA) and polyhexahydrotriazine (PHT) materials are described in general herein, as are potential methods for producing these materials. Further synthetic details and characterization of various example PHA and PHT materials are provided in commonly assigned, co-pending application Ser. No. 14/050,995, filed in the USPTO on Oct. 10, 2013, the entirety of which is incorporated herein by reference.

Methods for preparing polyhemiaminals (PHAs) and polyhexahydrotriazines (PHTs) include the reaction of aromatic diamines and paraformaldehyde. The PHAs and PHA films are stable intermediates in the preparation of the PHTs and PHT films, respectively. The PHAs are generally prepared at a temperature of about 20° C. to about 120° C., more, preferably at about 20° C. to about 100° C., and most preferably at about 40° C. to about 60° C. The PHAs form films when cast from a polar aprotic solvents (e.g., NMP), and the PHA films are stable at a temperature of about 20° C. to less than 150° C. The PHA films can have a Young's modulus of about 6 GPa, which is exceptionally high for an organic film.

The PHT films may be formed by thermally treating a PHA film at a temperature of at least 150° C., preferably about 165° C. to about 280° C., more preferably about 180° C. to about 210° C., and most preferably about 190° C. to about 210° C. for a period of time of about 1 minute to about 24 hours, and more preferably about 1 hour. The PHT films can have high heat resistance as measured by dynamic mechanical analysis (DMA). The PHT films can also have a high Young's modulus as measured by nanoindentation methods. In some instances, the Young's modulus of a PHT film can have a value in a range of about 8 GPa to about 14 GPa, exceeding that of bone (9 GPA).

Herein, a polyhemiaminal (PHA) is a crosslinked polymer comprising i) a plurality of trivalent hemiaminal groups of formula (1):

(1)

covalently linked to ii) a plurality of bridging groups of formula (2):

(2), wherein y' is 2 or 3, and K' is a divalent or trivalent radical comprising at least one 6-carbon aromatic ring. Herein, starred bonds represent attachment points to other portions of the chemical structure. Each starred bond of a given hemiaminal group is covalently linked to a respective one of the bridging groups. Additionally, each starred bond of a given bridging group is covalently linked to a respective one of the hemiaminal groups.

As an example, a polyhemiaminal can be represented herein by formula (3):

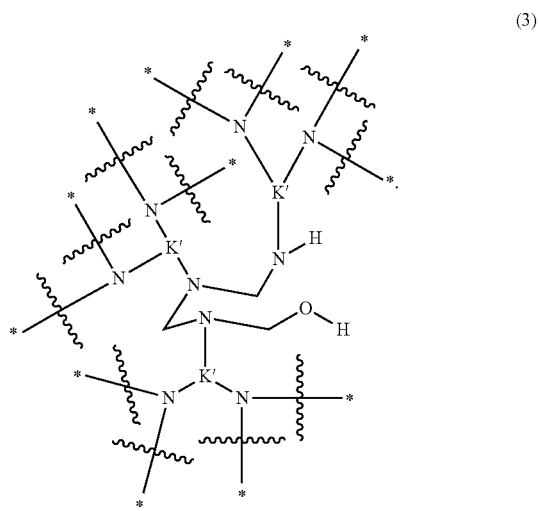

(3)

In this instance, each K' is a trivalent radical (y'=3) comprising at least one 6-carbon aromatic ring. It should be understood that each nitrogen having two starred wavy bonds in formula (3) is a portion of a different hemiaminal group.

The structure of formula (3) can also be represented using the notation of formula (4):

(4)

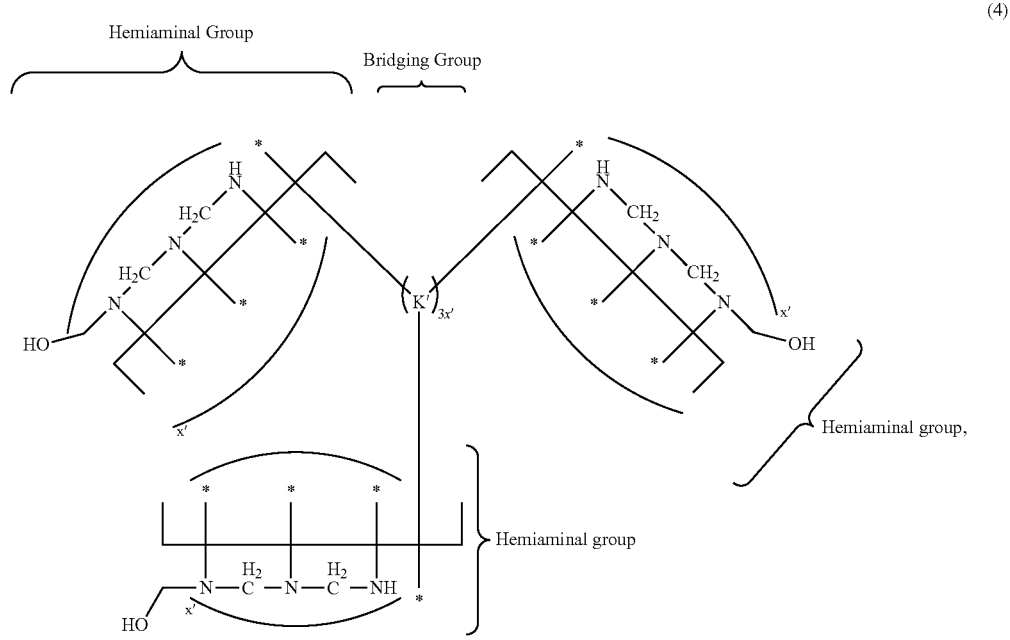

wherein x' is moles and each bridging group K' is a trivalent radical (y'=3 in formula (2)) comprising at least one 6-carbon aromatic ring. It should be understood that each starred nitrogen bond of a given hemiaminal group of formula (4) is covalently linked to a respective one of the bridging groups K'. Additionally, each starred bond of a given bridging group K' of formula (4) is covalently linked to a respective one of the hemiaminal groups.

Non-limiting exemplary trivalent bridging groups include:

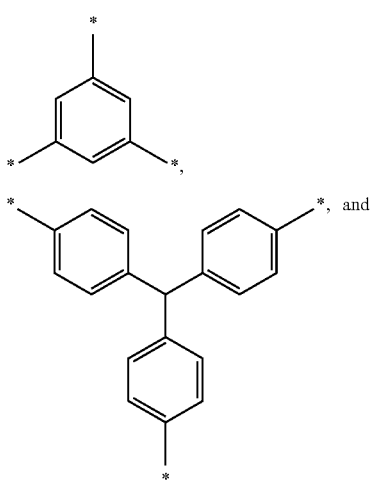

-continued

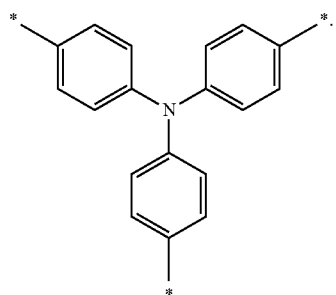

The bridging groups can be used singularly or in combination.

The remainder of the description discusses divalent bridging groups K'. It should be understood that the methods and principles below also apply to trivalent linking groups.

Polyhemiaminals composed of divalent bridging groups K' can be represented herein by formula (5):

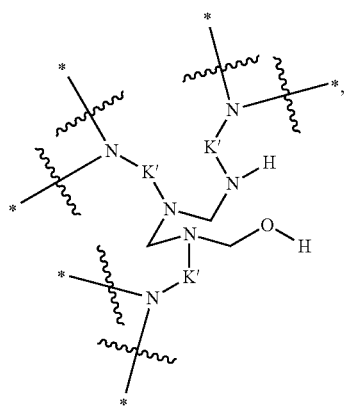

(5)

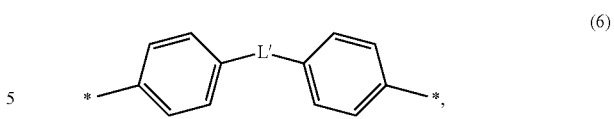

(6)

wherein L' is a divalent linking group selected from the group consisting of *—O—*, *—S—*, *—N(R')—*, *—N(H)—*, *—R"—*, and combinations thereof, wherein R' and R" independently comprise at least 1 carbon. In an embodiment, R' and R" are independently selected from the group consisting of methyl, ethyl, propyl, isopropyl, phenyl, and combinations thereof. Other L' groups include methylene (*—CH$_2$—*), isopropylidenyl (*—C(Me)$_2$-*), and fluorenylidenyl:

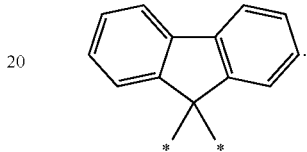

wherein K' is a divalent radical (y'=2 in formula (2)) comprising at least one 6-carbon aromatic ring. Each nitrogen having two starred wavy bonds in formula (5) is a portion of a different hemiaminal group.

More specific divalent bridging groups have the formula (6):

Polyhemiaminals composed of divalent bridging groups of formula (8) can be represented herein by formula (7):

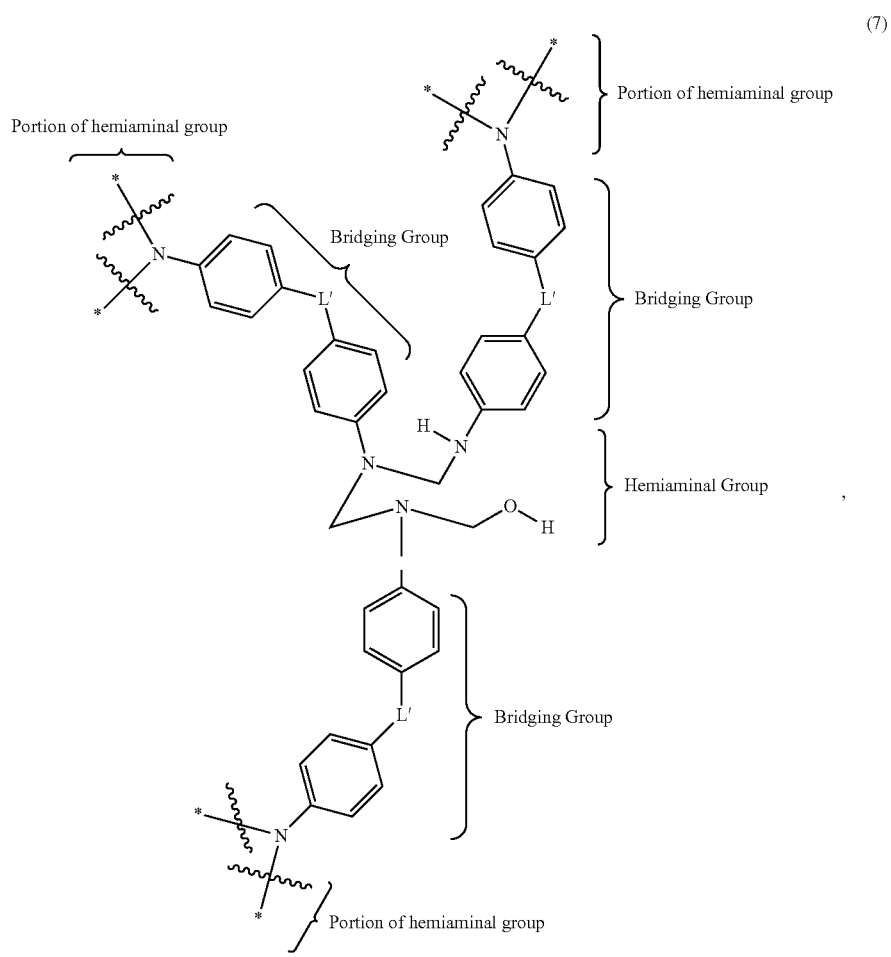

(7)

wherein L' is a divalent linking group selected from the group consisting of *—O—*, *—S—*, *—N(R')—*, *—N(H)—*, *—R"—*, and combinations thereof, wherein R' and R" independently comprise at least 1 carbon. Each nitrogen having two starred wavy bonds in formula (7) is a portion of a different hemiaminal group.

The polyhemiaminal of formula (7) can also be represented by the notation of formula (8):

covalently linked to ii) a plurality of divalent bridging groups K' (y'=2) of formula (2). Each starred bond of a given hexahydrotriazine group of formula (10) is covalently linked to a respective one of the bridging groups K'. Additionally, each starred bond of a given bridging group is covalently linked to a respective one of the hexahydrotriazine groups.

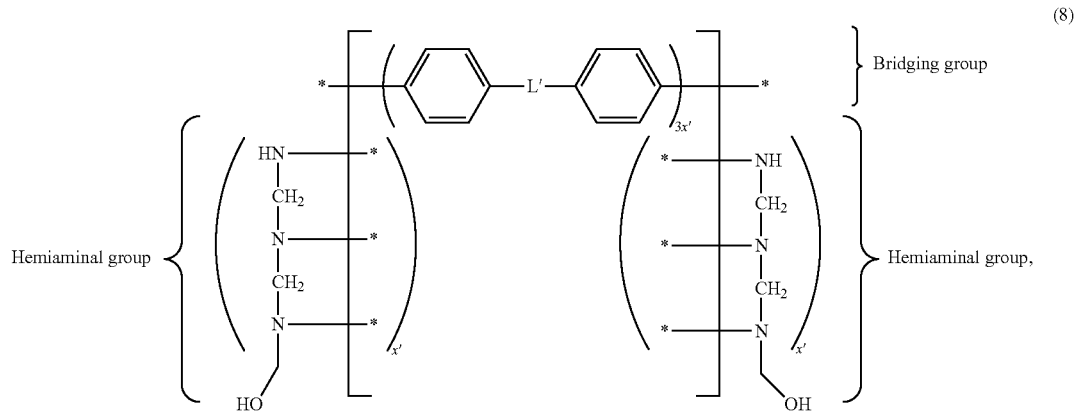

(8)

wherein x' is moles, and L' is a divalent linking group selected from the group consisting of *—O—*, *—S—*, *—N(R')—*, *—N(H)—*, *—R"—*, and combinations thereof, wherein R' and R" independently comprise at least 1 carbon. Each starred nitrogen bond of a given hemiaminal group of formula (8) is covalently linked to a respective one of the bridging groups. Additionally, each starred bond of a given bridging group of formula (8) is covalently linked to a respective one of the hemiaminal groups.

The hemiaminal groups can be bound non-covalently to water and/or a solvent. A non-limiting example is a hemiaminal group that is hydrogen bonded to two water molecules as shown in formula (9):

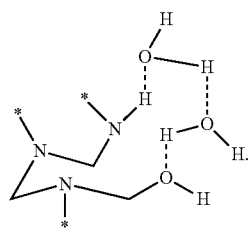

(9)

In an embodiment, a polyhexahydrotriazine (PHT) is a crosslinked polymer comprising i) a plurality of trivalent hexahydrotriazine groups of formula (10):

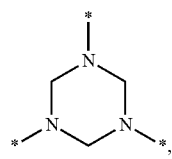

(10)

For PHTs comprising bridging groups of formula (6), the polyhexahydrotriazine is represented herein by formula (11):

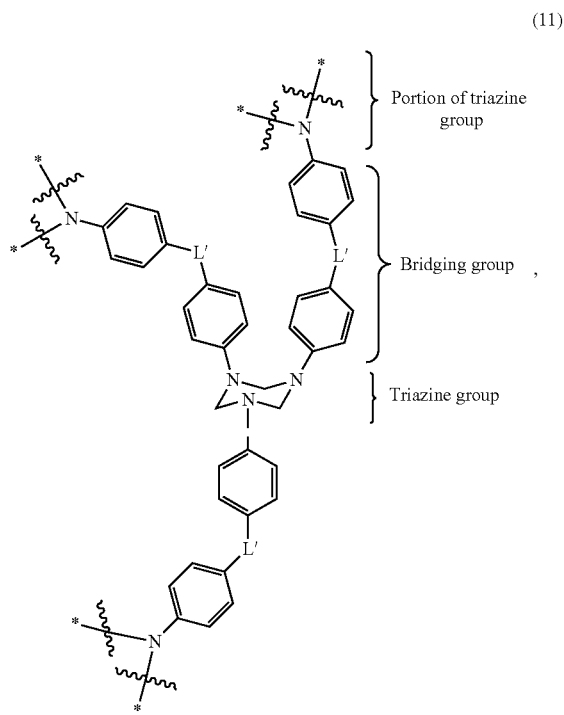

(11)

wherein L' is a divalent linking group selected from the group consisting of *—O—*, *—S—*, *—N(R')—*, *—N(H)—*, *—R"—*, and combinations thereof, wherein R' and R" independently comprise at least 1 carbon. Each nitrogen having two starred wavy bonds in formula (11) is a portion of a different hexahydrotriazine group.

The polyhexahydrotriazine is also represented herein by the notation of formula (12):

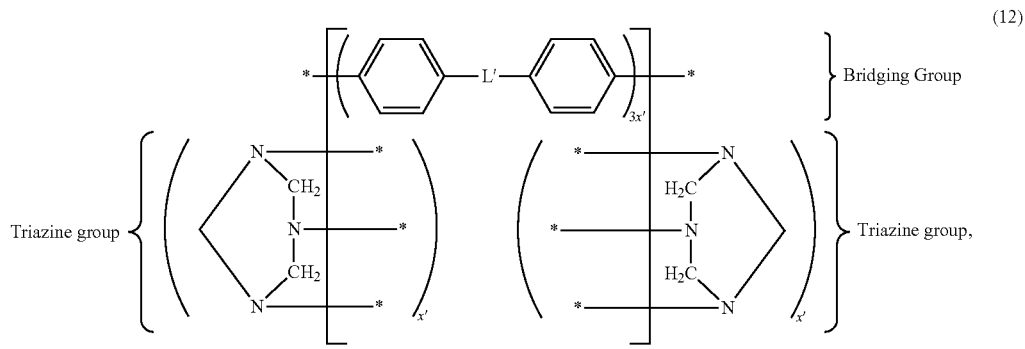

wherein x' is moles, L' is a divalent linking group selected from the group consisting of *—O—*, *—S—*, *—N(R)—*, *—N(H)—*, *—R"—*, and combinations thereof, wherein R' comprises at least 1 carbon and R" comprises at least one carbon. Each starred bond of a given hexahydrotriazine group of formula (12) is covalently linked to a respective one of the bridging groups. Additionally, each starred bond of a given bridging group of formula (12) is covalently linked to a respective one of the hexahydrotriazine groups.

The polyhexahydrotriazine can be bound non-covalently to water and/or a solvent (e.g., by hydrogen bonds).

Exemplary non-limiting divalent bridging groups include:

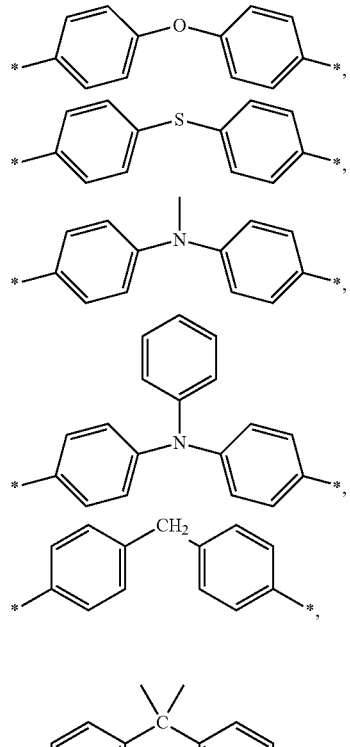

-continued

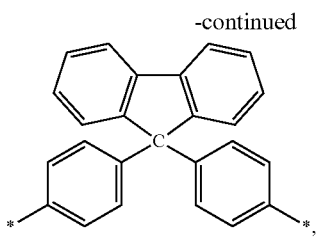

and combinations thereof.

The PHA and PHT can further comprise monovalent aromatic groups (referred to herein as diluent groups), which do not participate in chemical crosslinking and therefore can serve to control the crosslink density as well as the physical and mechanical properties of the PHA and PHT polymers. Monovalent diluent groups have a structure according to formula (13), formula (14), formula (15), and/or formula (16):

(13)

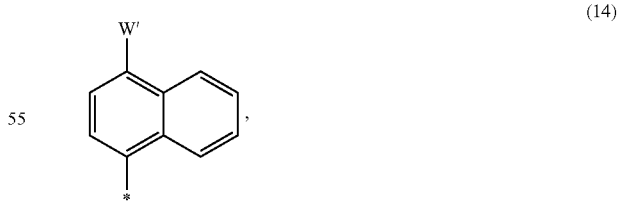

(14)

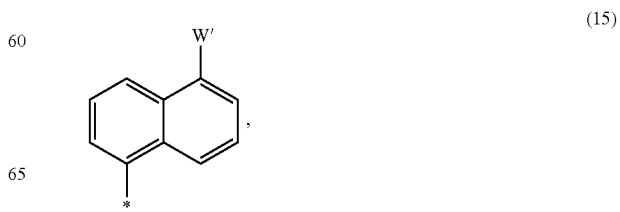

(15)

(16)

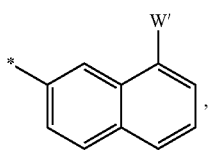

wherein W' is a monovalent radical selected from the group consisting of *—N(R¹)(R²), *—OR³, —SR⁴, wherein R¹, R², R³, and R⁴ are independent monovalent radicals comprising at least 1 carbon. The starred bond is linked to a nitrogen of a hemiaminal group or a hexahydrotriazine group.

Non-limiting exemplary diluent groups include:

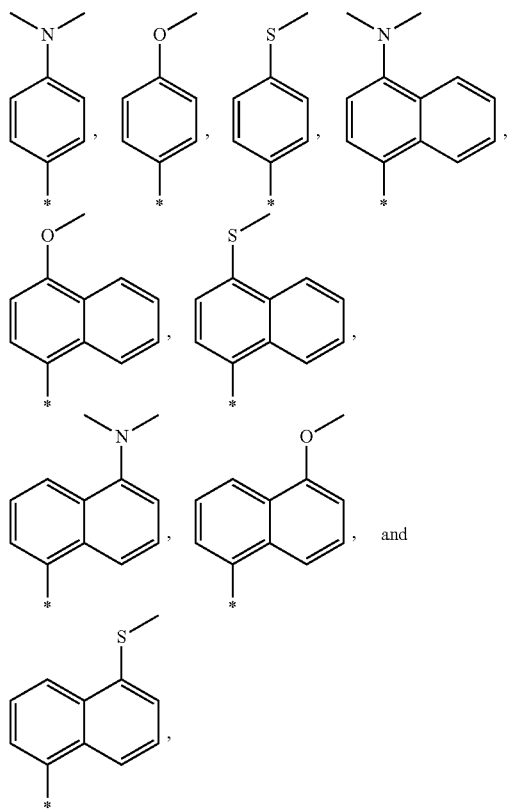

wherein the starred bond is linked to a nitrogen of a hemiaminal group or a hexahydrotriazine group. Diluent groups can be used singularly or in combination.

A method of preparing a polyhemiaminal (PHA) comprising divalent bridging groups comprises forming a first mixture comprising i) a monomer comprising two or more primary aromatic amine groups, ii) an optional diluent monomer comprising one aromatic primary amine group, iii) paraformaldehyde, and iv) a solvent. The first mixture is then preferably heated at a temperature of about 20° C. to about 120° C. for about 1 minute to about 24 hours, thereby forming a second mixture comprising the PHA. In an embodiment, the monomer comprises two primary aromatic amine groups.

The mole ratio of paraformaldehyde:total moles of primary aromatic amine groups (e.g., diamine monomer plus optional monoamine monomer) is preferably about 1:1 to about 1.25:1, based on one mole of paraformaldehyde equal to 30 grams.

Non-limiting exemplary monomers comprising two primary aromatic amine groups include 4,4'-oxydianiline (ODA), 4,4'-methylenedianiline (MDA), 4,4'-(9-fluorenylidene)dianiline (FDA), p-phenylenediamine (PD), 1,5-diaminonaphthalene (15DAN), 1,4-diaminonaphthalene (14DAN), and benzidene, which have the following structures:

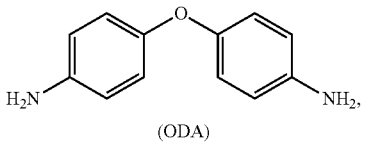

(ODA)

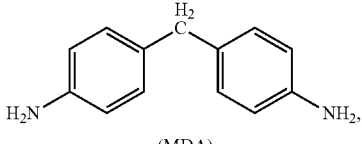

(MDA)

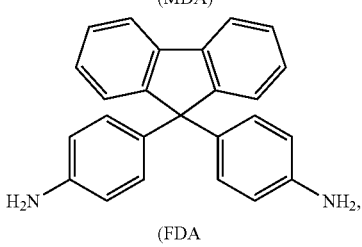

(FDA

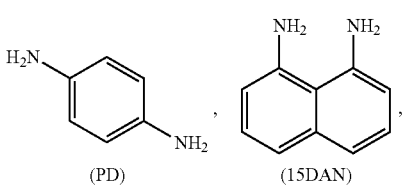

(PD)    (15DAN)

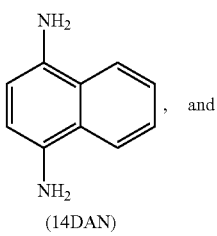

(14DAN)

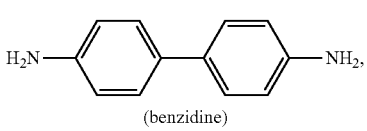

(benzidine)

Non-limiting exemplary diluent monomers include N,N-dimethyl-p-phenylenediamine (DPD), p-methoxyaniline (MOA), p-(methylthio)aniline (MTA), N,N-dimethyl-1,5-diaminonaphthalene (15DMN), N,N-dimethyl-1,4-diaminonaphthalene (14DMN), and N,N-dimethylbenzidene (DMB), which have the following structures:

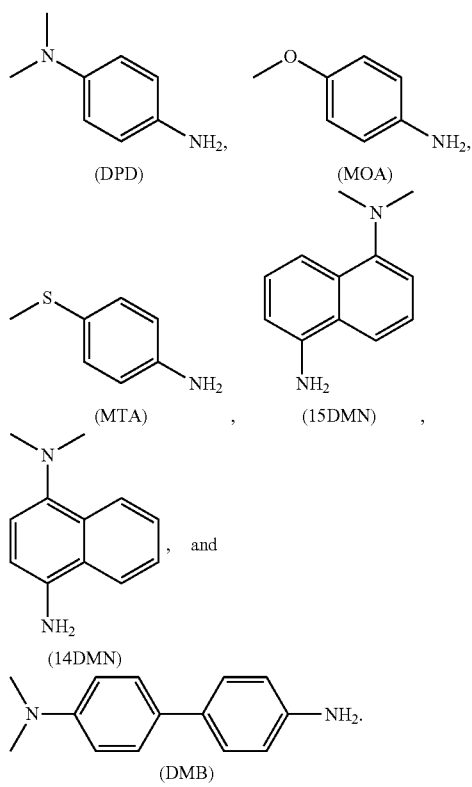

The diluent monomer can be used in an amount of 0 mole % to about 75 mole % based on total moles of monomer and diluent monomer.

The solvent can be any suitable solvent. Preferred solvents include dipolar aprotic solvents such as, for example, N-methyl-2-pyrrolidone (NMP), dimethylsulfoxide (DMSO), N,N-dimethylformamide (DMF), N,N-dimethylacetamide (DMA), Propylene carbonate (PC), and propylene glycol methyl ether acetate (PGMEA). Most preferably, the solvent is NMP.

A method of preparing a polyhexahydrotriazine (PHT) having divalent bridging groups comprises forming a first mixture comprising i) a monomer comprising two aromatic primary amine groups, ii) an optional diluent monomer comprising one aromatic primary amine group, iii) paraformaldehyde, and iv) a solvent, and heating the first mixture at a temperature of at least 150° C., preferably about 165° C. to about 280° C., thereby forming a second mixture comprising a polyhexahydrotriazine. The heating time at any of the above temperatures can be for about 1 minute to about 24 hours.

Alternatively, the PHT can be prepared by heating the solution comprising the PHA at a temperature of at least 150° C., preferably about 165° C. to about 280° C. even more preferably at about 180° C. to about 220° C., and most preferably at about 200° C. for about 1 minute to about 24 hours.

A polyhemiaminal film can be prepared from a mixture comprising a polyhemiaminal and a solvent prepared as described above is disposed on a surface of a substrate, thereby forming structure comprising an initial film layer comprising the polyhemiaminal, solvent and/or water disposed on the covered surface of substrate. The initial film layer is heated at a temperature of about 20° C. to about 120° C. for about 1 minute to about 24 hours, thereby forming a structure comprising a polyhemiaminal (PHA) film layer that is disposed on the surface of substrate. The PHA film layer may be substantially free of solvent and/or water.

The substrate can be any suitable substrate, in particular any substrate whose Young's modulus is a factor of 5 greater than the polyhemiaminal and/or polyhexahydrotriazine. Non-limiting examples of these materials include semiconductor wafers (e.g., silicon wafers), most metals, refractory materials, and other polymers.

The solvent mixture containing the PHA can be cast onto the substrate using any suitable coating technique (e.g., spin coating, dip coating, roll coating, spray coating, and the like).

A polyhexahydrotriazine (PHT) film may be prepared from a PHA film. A polyhemiaminal film layer on a substrate can be heated at a temperature of at least 150° C., preferably about 165° C. to about 280° C. even more preferably at about 180° C. to about 220° C., and most preferably at about 200° C., thereby forming a structure comprising polyhexahydrotriazine (PHT) film layer disposed on the substrate. The heating time at any of the above temperatures can be about 1 minute to about 24 hours. The PHT film layer thus formed may be substantially free of solvent and water. The hemiaminal groups of the PHA film may be substantially or wholly converted to hexahydrotriazine groups by heating the PHA film at a temperature in this range.

The number average molecular weight (Mn) of the PHA and/or PHT polymers can be in a range of 1000 to 100,000, preferably in a range of 1000 to 50,000, and most preferably in a range of 1000 to 20,000.

The various polyhexahydrotriazines are attractive for applications requiring lightweight, rigid, strong thermosets such as aerospace engineering, electronics, and as mixtures for increasing the modulus of known resins and composites.

Sequestration of Sulfur Compounds

With reference now to FIG. 1, a PHT material may react with a sulfur compound as depicted. In this instance, the sulfur compound is $H_2S$, but thiol compounds will also react with a PHT material. Under some reaction conditions various sulfur allotropes, such as octosulfur ($S_8$, also referred to as cyclo-sulfur), may also react with PHT materials.

In the reaction depicted in FIG. 1, the sulfur atoms replace two of three nitrogen atoms in the hexahydrotriazine moiety, which results in two divalent linking groups (also referred to as the bridging group) being separated from (that is, no longer covalently bonded to) the hexahydrotriazine (HT) moiety. The reaction of the PHT material with a sulfur compound thus results in incorporation of sulfur atoms into the PHT material. As such, PHT materials can be used as a reactive filtration media to remove sulfur compounds from various fluids.

Figure 2:
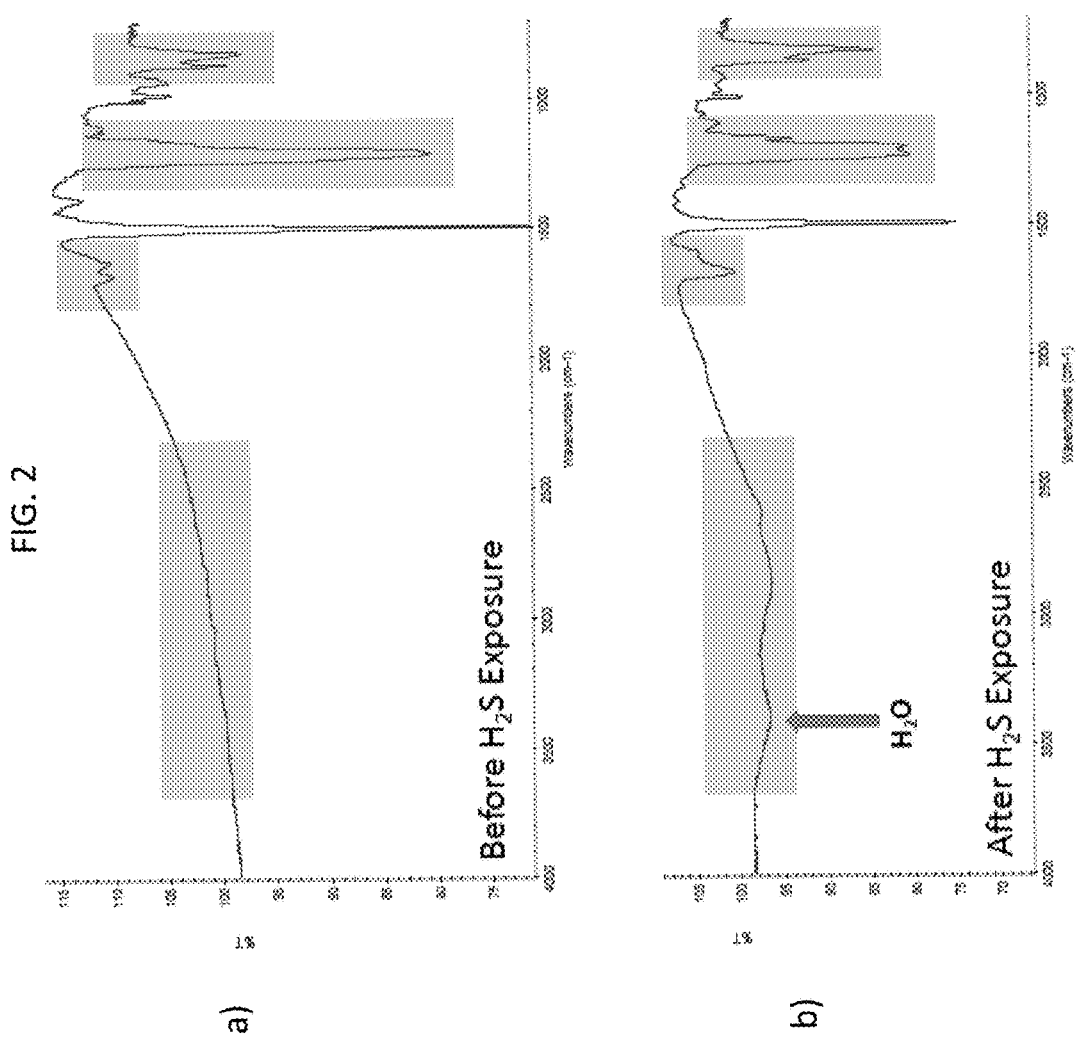
FIG. 2 depicts a Fourier-transform infrared (FT-IR) spectrograph of a PHT material before (a) and after (b) exposure to a sulfur compound.

FIG. 2 depicts a Fourier-transform infrared (FT-IR) spectrograph of a PHT material before (a) and after (b) exposure to a sulfur compound, which in this instance is $H_2S$. The alteration in the before (a) and after (a) spectra establishes, in general, a reaction occurs between the PHT material and $H_2S$.

As a means to understand the reaction between PHT materials and sulfur compounds, studies on small molecule model compounds have been performed. In general, the small molecule model compounds incorporate a hexahydrotriazine group, but are not polymeric. Reactions of the small molecule model compounds are typically easier to monitor and detect under controlled conditions.

Figure 3:
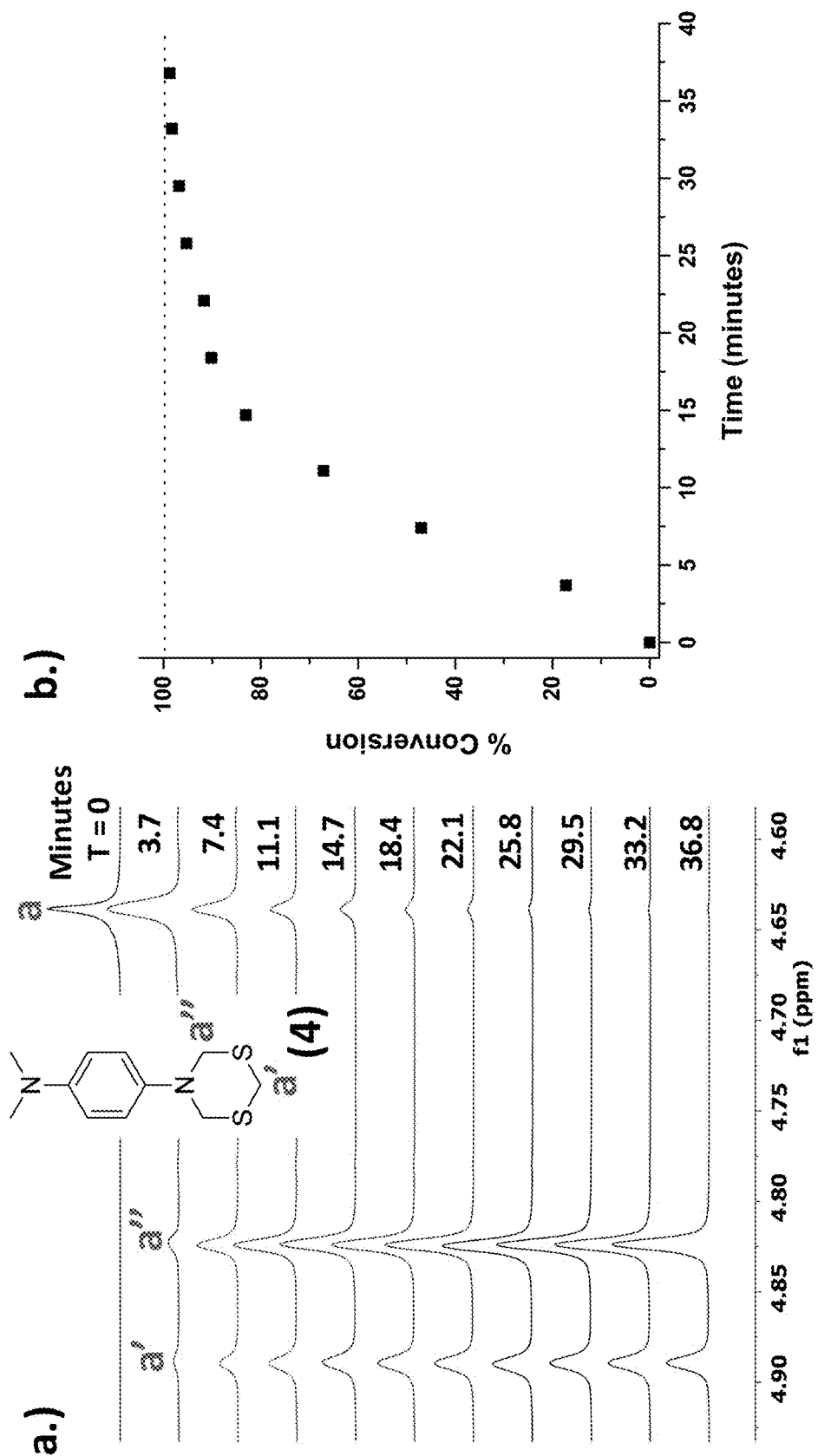
FIG. 3 depicts a) $^1$H-NMR spectra of a reaction of a small molecule model compound having a hexahydrotriazine moiety and a sulfur compound, and b) a kinetic profile of the reaction the small molecule model compound and the sulfur compound.

FIG. 3 depicts $^1$H-NMR spectra of a reaction between a sulfur compound ($H_2S$) and small molecule model compound including a hexahydrotriazine moiety (4,4',4"-(1,3,5- triazinane-1,3,5-triyl)tris(N,N-dimethylaniline)) (also referred to as SMC-HT). FIG. 3 shows several NMR spectra obtained over time (with a 3.7 minute spacing).

In FIG. 3, the diagnostic singlet (a) corresponding to a hydrogen on the nitrogen-rich HT core is observed to decrease in intensity during the course of the reaction, while two new peaks (a') and (a") increase in intensity. The peaks (a') and (a") are considered to correspond to the hydrogen atoms on the diothiazine reaction product.

FIG. 3 also depicts the kinetic profile of the reaction between the small molecule compound (SMC-HT) and $H_2S$. The data in the kinetic profile is based on the $^1$H-NMR measurements. After a period of approximately 37 minutes, the peak (a) is no longer observed in the spectrum, indicating substantially complete conversion of SMC-HT into a different compound, specifically a diothiazine compound in which two sulfur atoms have been incorporated in place of two ring nitrogens of the original SMC-HT. The triathiane product (corresponding to a reaction product in which all ring nitrogens in the SMC-HT are replaced with sulfur atoms) has not been observed experimentally under the studied reaction conditions; however, preliminary density functional theory calculations suggest the formation of triathiane is thermodynamically favorable. Based on these preliminary results it is possible the formation of the triathiane product is kinetically disfavored over the two-sulfur (diothiazine) reaction product.

Figure 4:
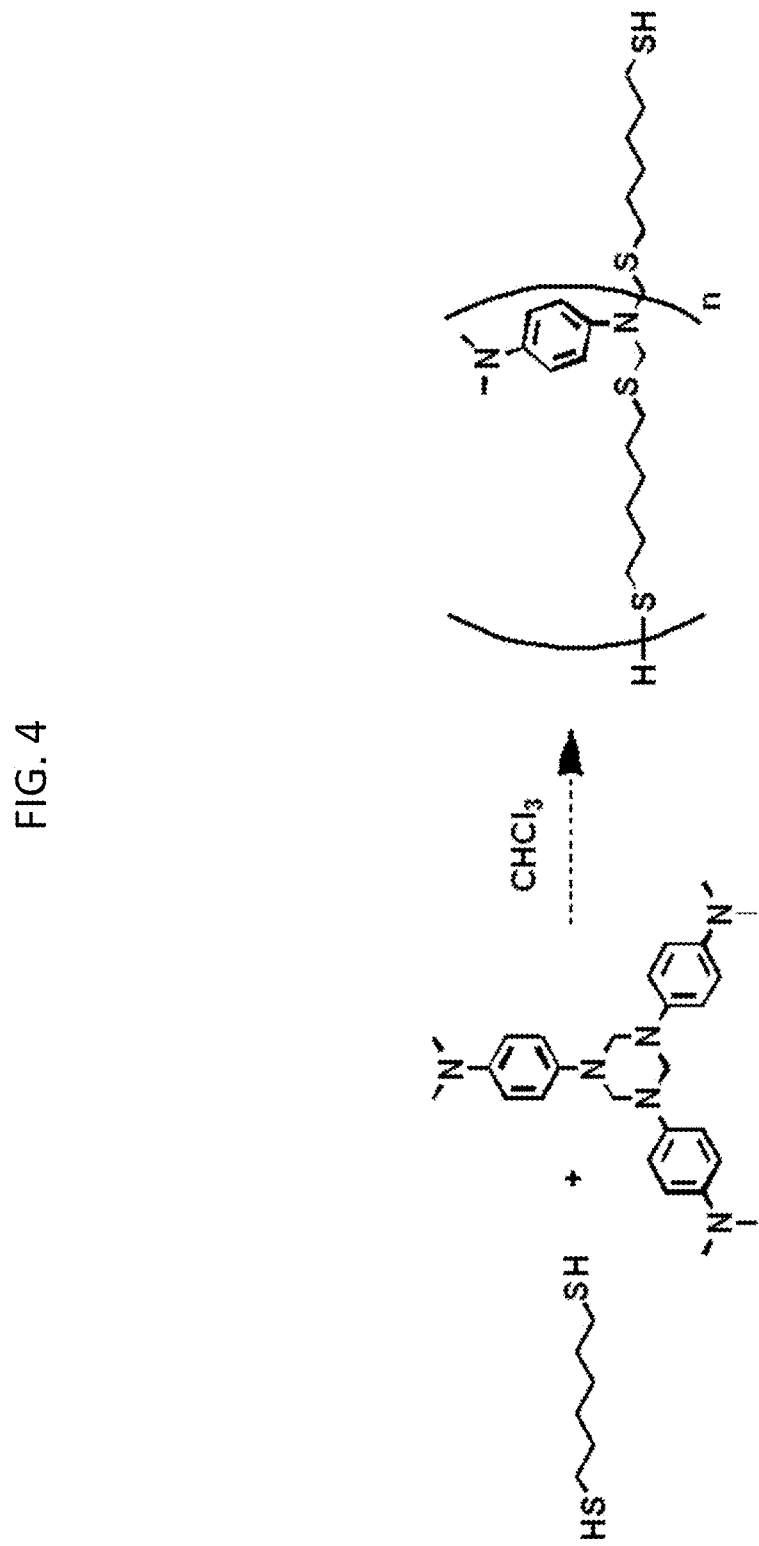
FIG. 4 depicts a reaction between a PHT-type material and a thiol compound.

FIG. 4 depicts a reaction process between a PHT material and a thiol. Via the depicted reaction process thiols may be incorporated into the PHT material. While a specific thiol (hexan-1,6-dithiol) is depicted in FIG. 4, other thiols would be expected to react similarly. The reaction between PHT materials and thiols can be used to remove thiol compounds from various fluids, but it should also be noted that the reaction may also be effectively used to produce modified PHT materials which include a thioether linkage.

While the above description of the reaction schemes resulting in incorporation of sulfur have focused on reactions between PHT materials and sulfur compounds, PHA materials are also expected to react with sulfur compounds. Without being limited to any particular reaction mechanism, it should be noted that at elevated temperatures PHA materials will convert to PHT materials, thus reaction of PHA materials with sulfur compounds may proceed through a PHT intermediate at elevated temperatures (e.g., 150° C. to 280° C.).

Removal of Sulfur Compounds from Fluids

As described, PHA and PHT materials react with sulfur compounds in such a way that sulfur becomes incorporated into the polymeric matrices by covalent linkages. As such, PHA and PHT materials can be used as reactive filter media for removal of sulfur compounds from fluids. Such filtration media can be incorporated in a fixed-media filter device such as an air intake filter for microelectronic fabrication facility or other pollution sensitive environment, an automotive fuel filter, an automotive oil filter, a water treatment filter, a combustion exhaust filter, or the like.

The filtration media may alternatively be added as particulates to the fluid from which sulfur compounds are to be removed. The added particulates and the fluid may later be separated by various methods, such as, for example, fixed-filter filtration, settling, centrifuge, solvent partitioning, evaporative methods, distillation, or the like. The filter media particulates may in some embodiments be included in a fluidized bed apparatus—that is, the fluid to be filtered and the particulate filter media may be contacted with each other under flow and pressure conditions which cause the fluid-particulate mixture to behave similarly to a fluid (fluidize).

Figure 5:
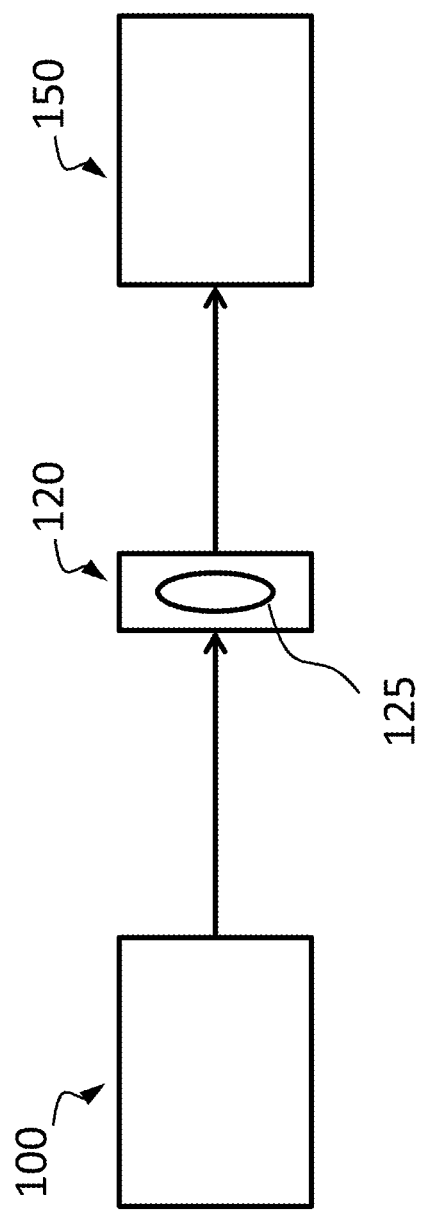
FIG. 5 depicts a filter comprising a filter medium including at least one of a PHT material and a polyhemiaminal (PHA) material.

FIG. 5 depicts a filtration system 120 including a filter media 125. Filtration system 120 receives a fluid from source 100. The fluid is filtered by contact with filter media 125 in filtration system 120. Filter media 125 may include a PHT material, PHA material, or both a PHT and a PHA material. Filter media 125 may in some embodiments include various combinations of different PHT materials and PHA materials. After the fluid is filtered, it may be received in environment 150.

Source 100 may be anything that supplies, outputs, generates, or contains a fluid including sulfur compounds. For example, source 100 may be a crude oil reservoir, a natural gas storage basin, a liquefied natural gas (LNG) production facility, a petroleum refinery, petrochemical plant, or the like, which collectively may be referred to as a hydrocarbon processing facility.

Crude oil and natural gas deposits typically contain sulfur compounds such as $H_2S$ and mercaptans at undesirable levels. For crude oils, sulfur compound levels must be lowered during the refining process to meet customer and regulatory requirements for end-use fuels and lubricants. For natural gas, sulfur levels often must be reduced prior to storage or transport because sulfur compounds will promote corrosion of components of pipelines, storage tank, and processing equipment. Sulfur-based air pollution from the combustion of natural gas may also be of concern and require reductions in sulfur levels in natural gas feed stocks prior to combustion.

In some embodiments, source 100 may include a power plant burning hydrocarbon fuel (e.g., natural gas, oil, and coal) which contains sulfur. The power plant outputs combustion exhaust streams including sulfur-based air pollutants such as $H_2S$ found in or derived from the hydrocarbon fuel. Source 100 may similarly be a combustion engine or a boiler found in a vehicle burning hydrocarbon fuels (e.g., gasoline, kerosene, diesel fuel) including sulfur compounds, and thus consequently outputs combustion exhaust streams including sulfur-based air pollutants. In such instances, filtration system 120 may be referred to as an exhaust gas filter and such a system may be used to reduce sulfur-based air pollutants from in the combustion exhaust gas.

Source 100 may also be a fuel storage tank of a vehicle (e.g., automobile, boat, ship, diesel locomotive, motorcycle, airplane, helicopter, etc.) having a combustion engine or a boiler burning fuels including sulfur compounds. In such instances, filtration system 120 may be referred to as a fuel filter and may serve to reduce air pollution or engine/boiler corrosion by reducing sulfur compound levels in fuels prior to combustion. Similarly, source 100 may be an oil reservoir of a vehicle having an internal combustion engine. In such instances, the filtration system 120 may be referred to as an oil filter.

Source 100 may also be the open atmosphere. Sulfur-based air pollution on occasion may be at levels which are too high for prolonged exposure by humans, animals, or corrosion sensitive materials such as electronic equipment. In these instances, air handling equipment may incorporate filtration system 120 to provide clean air to environment 150.

Environment 150 may, in general, be anything receiving the filtered fluid from filtration system 120. Environment 150 may be the open atmosphere, when, for example, source 100 is a combustion engine or a power plant. When source 100 is the open atmosphere, environment 150 may be a pollution sensitive environment such as a semiconductor device fabrication facility, a microelectronic device manufacturing facility, a data storage center, a server room, a server farm, a electronic component warehouse, a hospital ward, archival storage facility, or portions thereof. When source 100 is a crude oil reservoir or natural gas basin, environment 150 may be, for example, a crude oil storage tank, a refinery, a natural gas storage basin, a LNG processing plant, a pipeline, a petrochemical plant, or portions thereof.

In an embodiment, filter medium 125 may comprise a plurality of fibers. In a further embodiment, the plurality of fibers may comprise a fibrous mat or a mass of fibers. In some embodiments, the plurality of fibers comprising the filter medium may include fibers coated with at least one of a PHT and a PHA. In some embodiments, the plurality of fibers comprising the filter medium are themselves formed from PHA or PHT.

The PHT and/or PHA material in filtration system 120 may be provided, without limitation, as one or more coating on a substrate, a film (whether on a substrate or not), a membrane, a powder, a resin, a fiber, and/or a system of fibers. In this context, a system of fibers includes, without limitation, such things as a felt, a fibrous mat, a fabric, a mesh, and a cloth. A system of fibers may be woven, twisted, knitted, felted, or otherwise may be any coordination or any agglomeration of individual fibrous elements whether such coordination or agglomeration is systematic, chaotic, or random. Fibers in this context includes, without limitation, filaments, threads, yarns, and strings.

Figure 6:
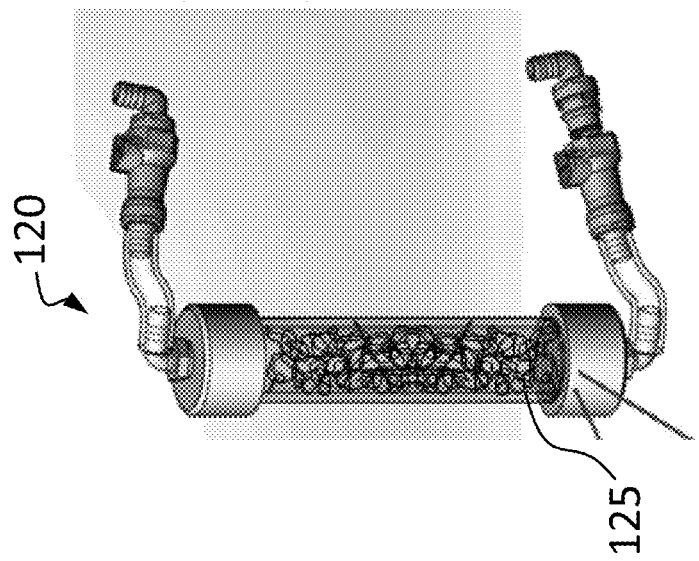
FIG. 6 depicts a filter including a filter medium including at least one of a PHT material and a PHA material.

FIG. 6 depicts an example embodiment of a filtration system 120 including a filter medium 125 comprising a plurality of fibers. Fiber lengths and diameters in conjunction with overall media density may be set as appropriate in consideration of the fluid flow properties, pressure drop limitations, and desired post-filtration contaminant levels. The fibers may be nano-scale fibers (nanofibers) with diameters less than 1 micron or may be macro-scale fibers directly visible to the human eye. The filter media 125 may provide tortuous fluid flow pathways to promote filtration of generic particulates from the fluid in addition to reactive filtration of sulfur compounds.

Figure 7:
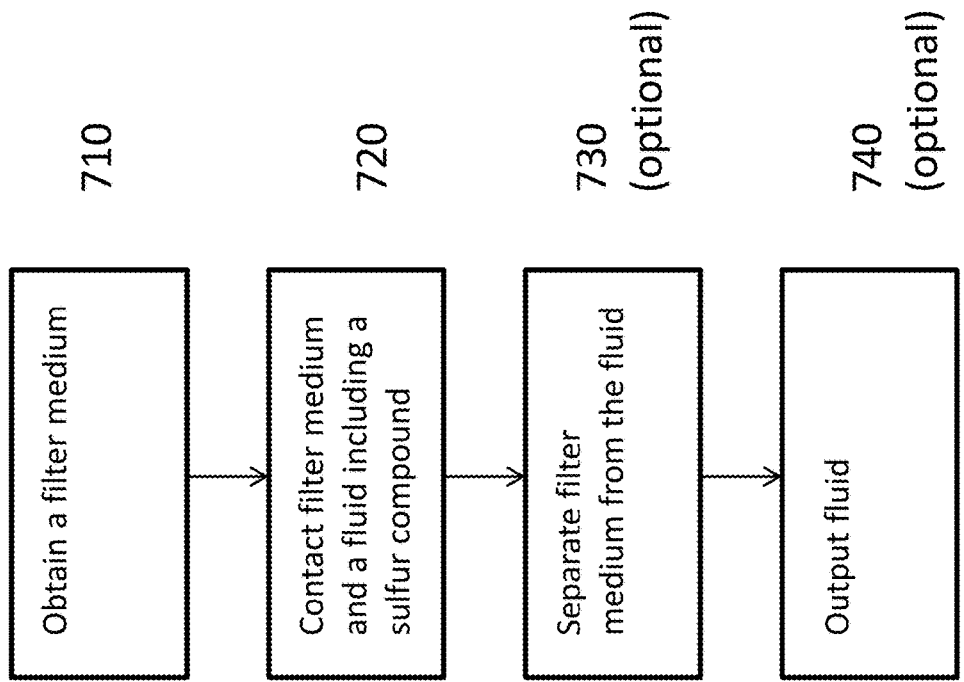
FIG. 7 is a flowchart depicting a method of removing sulfur compounds from a fluid.

FIG. 7 depicts a method 700 for removing sulfur compounds from a fluid. In element 710 of the method, a filtration medium including at least one of a PHA and a PHT material is obtained.

In an embodiment of method 700, the filter medium may be incorporated in a filtration system 120 such as depicted in FIG. 6. In element 720 of the method, the filtration medium and the fluid are placed in contact with each other. When the filtration medium is incorporated in a fixed filtration system 120, or the like, contact generally involves passing the fluid through the filtration system 120. This may require pumps, gas compressors, or similar equipment to provide a necessary pressure differential between the intake point and the output point of the filtration system to induce fluid flow. The heating or cooling of the fluid may also be necessary, depending on the source of the fluid. For example, combustion exhaust gas from a power plant may initially be at a very high temperature and it may be preferable to reduce the temperature before contact with the filtration medium 125.

When a fixed filtration system 120 is used, element 730 of the method may be accomplished as a matter of course when the fluid is output in element 740 of the method to the environment from the filtration system 120 because generally, filtration media 125 will be retained within filtration system 120.

In another embodiment of method 700, element 720 may include adding or mixing a filtration medium comprising particles of a PHA material or a PHT material. For example, the fluid to be filtered may be contained in a storage tank or reaction vessel and a particulate filtration medium could simple be dumped in to the tank or vessel. Depending on particulate size and fluid density it may be advantageous to physically mix or stir the fluid. Once the filtration media as been placed in contact with the fluid sulfur sequestering reactions will occur as described previously and sulfur will be incorporated into the particulate filtration media. The filtration media in this instance can be a mixture of different PHA and PHT compounds or a single compound. The sulfur compound levels in the fluid can be optionally monitored to determine the progress of the filtration process.

After the filtration media has been mixed with the fluid, as indicated in element 730 the filtration media may be separated from the fluid. The separation process may be optional in some embodiments, for example, when the fluid is a crude oil being prepared for shipment in a pipeline or by a tanker, it may be sufficient for purposes of corrosion prevention to bind the sulfur compounds to the filtration media to reduce the availability of the sulfur contaminants in corrosive reactions.

When element 730 is considered necessary, the separation may be performed by various methods, such as settling, centrifuge, evaporative distillation, solvent partitioning, or the like, before output of the fluid in element 740.

Corrosion Prevention Coatings

While in many instances it may be possible to remove sulfur compounds from a fluid and thereby reduce sulfur-induced corrosion caused by exposure to the fluid, it is not always possible to provide only filtered fluids to systems or expose corrosion sensitive components only to filtered fluids. In addition, filtration systems may simply fail on occasion or otherwise be inadequate to the task of providing the necessary reduction in corrosive components. With this in mind, it may be preferable to provide a protective coating on corrosion sensitive components.

PHA and PHT coatings may be formed on components by a variety of techniques. For example, a solvent mixture containing a PHA material can be cast onto the component using spin coating, dip coating, roll coating, brush coating, spray coating, and the like. A PHA film can be converted to a PHT film by heating. PHT coatings may also be directly formed on a component using spin coating, dip coating, roll coating, brush coating, spray coating, and the like.

In an embodiment, the component to be protected is a pipeline component, crude oil or natural gas processing equipment or portions thereof, an interior surface of a crude oil storage tank, a LNG storage tank, and the like.

In another embodiment, the component may be an electronic component, a circuit board, a hard disk drive platter, a semiconductor device, a micro-electromechanical system (MEMS), a light emitting diode device, or a portion thereof. Sulfur induced corrosion of electronic components is known to be problematic in urban settings with high atmospheric pollution levels. The applied coating in this embodiment may be a conformal coating and be used in place of or in addition to silicone-based coatings which are presently used for microelectronic applications. The excellent thermal stability of PHT materials makes them suitable for coating electronic components exposed to high temperatures (e.g., greater than 180° C.) or otherwise operating at high temperatures.

The applied thickness of the coating may vary depending on various factors such as expected component lifetime, thermal conditions, expected physical abrasiveness of the operating environment of the component, value of the component and its corrosion tolerance. A coating thickness from about 100 nm to about 500 microns or greater may be adopted.

Figure 8:
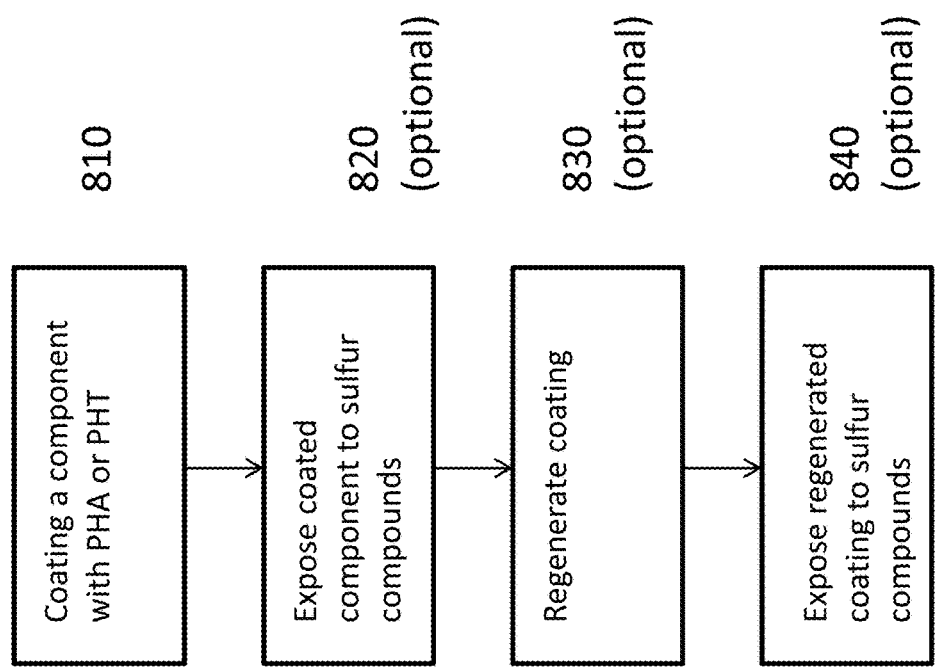
FIG. 8 is a flowchart depicting a method for protecting a component from corrosion.

FIG. 8 depicts a method 800 of reducing corrosion of a component. In element 810 of the method, a component is coated with a PHA material or a PHT material. The thickness of the coating may be any suitable thickness and the component may be, without limitation, a portion of hydrocarbon (e.g., oil, natural gas, LNG) production facility, a microelectronic component, a circuit board, a portion of automobile.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

While the foregoing is directed to embodiments of the present invention, other and further embodiments of the invention may be devised without departing from the basic scope thereof, and the scope thereof is determined by the claims that follow.

What is claimed is:

1. A filter, comprising:
a filtration medium including:
a polyhexahydrotriazine (PHT) material including:
a plurality of trivalent hexahydrotriazine groups having the structure:

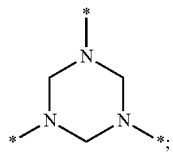

and
a plurality of divalent bridging groups of formula:

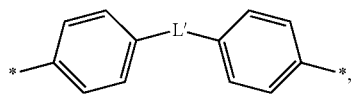

wherein
L' is a divalent linking group selected from the group consisting of —O—, —S—, —N(R')—, —N(H)—, —R"—, and combinations thereof, R' comprises at least 1 carbon and R" comprises at least one carbon, each starred bond of a trivalent hexahydrotriazine group in the plurality of trivalent hexahydrotriazine groups is covalently linked to a different respective divalent bridging group in the plurality of divalent bridging groups at a starred bond of the respective divalent bridging group.

2. The filter of claim 1, wherein the filtration medium consists of the PHT material.

3. The filter of claim 1, wherein the filtration medium comprises a plurality of fibers.

4. The filter of claim 3, wherein the plurality of fibers comprise a fibrous mat.

5. The filter of claim 3, wherein the PHT material is coated onto the plurality of fibers.

6. The filter of claim 3, wherein fibers of the plurality of fibers are formed of the PHT material.

7. The filter of claim 1, wherein filtration medium is in a fluidized bed.

8. A filter, comprising:
a filtration medium including:
a polyhemiaminal (PHA) material including:
a plurality of trivalent hemiaminal groups having the structure:

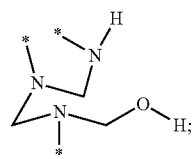

and
a plurality of divalent bridging groups of formula:

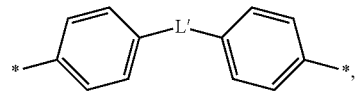

wherein
L' is a divalent linking group selected from the group consisting of —O—, —S—, —N(R')—, —N(H)—, —R"—, and combinations thereof, wherein R' comprises at least 1 carbon and R" comprises at least one carbon, each starred bond of a trivalent hemiaminal group in the plurality of trivalent hemiaminal groups is covalently linked to a different respective divalent bridging group in the plurality of divalent bridging groups at a starred bond of the respective divalent bridging group.

9. The filter of claim 8, wherein the filtration medium consists of the PHA material.

10. The filter of claim 8, wherein the filtration medium comprises a plurality of fibers.

11. The filter of claim 10, wherein the plurality of fibers comprise a fibrous mat.

12. The filter of claim 10, wherein the PHA material is coated onto the plurality of fibers.

13. The filter of claim 10, wherein fibers in the plurality of fibers are formed of the PHA material.

14. The filter of claim 8, wherein filtration medium is in a fluidized bed.

15. A filter, comprising:
a filtration medium including:
a polyhexahydrotriazine (PHT) material including:
a plurality of trivalent hexahydrotriazine groups having the structure:

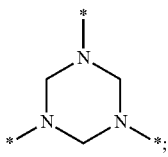

and
a first plurality of divalent bridging groups of formula:

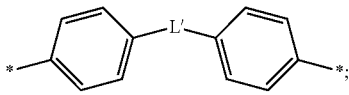

and
a polyhemiaminal (PHA) material including:
a plurality of trivalent hemiaminal groups having the structure:

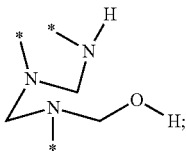

and
a second plurality of divalent bridging groups of formula:

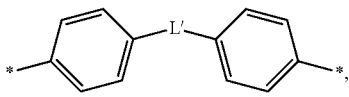

wherein,
in each instance, L' is a divalent linking group selected from the group consisting of —O—, —S—, —N(R')—, —N(H)—, —R"—, and combinations thereof, R' comprises at least 1 carbon and R" comprises at least one carbon, each starred bond of a trivalent hexahydrotriazine group in the plurality of trivalent hexahydrotriazine groups is covalently linked to a different respective divalent bridging group in the first plurality of divalent bridging groups at a starred bond of the respective divalent bridging group in the first plurality, each starred bond of a trivalent hemiaminal group in the plurality of trivalent hem iaminal group is covalently linked to a starred bond of a different respective divalent bridging groups in the second plurality of divalent bridging groups, and each starred bond of a given bridging group is linked to a respective one of the hemiaminal groups at a starred bod of the respective divalent bridging group in the second plurality.

16. The filter of claim 15, wherein the filtration medium comprises a plurality of fibers.

17. The filter of claim 16, wherein the plurality of fibers comprise a fibrous mat.

18. The filter of claim 16, wherein at least one of the PHT material and the PHA material is coated onto the plurality of fibers.

19. The filter of claim 16, wherein fibers in the plurality of fibers are formed of at least one of the PHT material and the PHA material.

20. The filter of claim 15, wherein filtration medium is in a fluidized bed.